United States Patent
Wade (10) Patent No.: US 11,857,154 B2
(45) Date of Patent: Jan. 2, 2024

(54) SYSTEMS AND METHODS FOR CLOSED-LOOP SURGICAL IMAGING OPTIMIZATION

(71) Applicant: Jack Wade, La Jolla, CA (US)

(72) Inventor: Jack Wade, La Jolla, CA (US)

( * ) Notice: Subject to any disclaimer, the term of this patent is extended or adjusted under 35 U.S.C. 154(b) by 0 days.

(21) Appl. No.: 17/732,479

(22) Filed: Apr. 28, 2022

(65) Prior Publication Data
US 2022/0369911 A1    Nov. 24, 2022

Related U.S. Application Data

(63) Continuation of application No. 15/729,130, filed on Oct. 10, 2017, now abandoned.

(60) Provisional application No. 62/406,216, filed on Oct. 10, 2016.

(51) Int. Cl.
| | |
|---|---|
| *A61B 1/00* | (2006.01) |
| *A61B 1/06* | (2006.01) |
| *A61B 90/30* | (2016.01) |
| *A61B 34/00* | (2016.01) |
| *A61B 1/07* | (2006.01) |
| *A61B 1/045* | (2006.01) |

(Continued)

(52) U.S. Cl.
CPC .... *A61B 1/000095* (2022.02); *A61B 1/00009* (2013.01); *A61B 1/00013* (2013.01); *A61B 1/04* (2013.01); *A61B 1/045* (2013.01); *A61B 1/0638* (2013.01); *A61B 1/0655* (2022.02); *A61B 1/07* (2013.01); *A61B 34/25* (2016.02); *A61B 90/37* (2016.02); *A61B 2090/306* (2016.02); *A61B 2090/3614* (2016.02); *A61B 2090/371* (2016.02)

(58) Field of Classification Search
CPC ............ A61B 1/00009; A61B 1/00006; A61B 1/00004; A61B 1/00043; A61B 1/0638; A61B 1/06; A61B 34/25; A61B 90/36; A61B 90/37; A61B 2090/306; A61B 2090/373

See application file for complete search history.

(56) References Cited

U.S. PATENT DOCUMENTS

| | | | | |
|---|---|---|---|---|
| 4,672,683 A | * | 6/1987 | Matsueda | ............... G06F 16/58 |
| | | | | 382/128 |
| 5,001,556 A | * | 3/1991 | Nakamura | ........... H04N 5/2354 |
| | | | | 348/E5.029 |

(Continued)

*Primary Examiner* — John P Leubecker
(74) *Attorney, Agent, or Firm* — Olivo IP Law Group, P.C.; John W. Olivo, Jr.

(57) ABSTRACT

The disclosed technology relates to closed-loop medical imaging for a medical environment. Various embodiments provide for a surgical camera, such as an endoscopic camera, comprising one or more image sensors. The image sensors may be configured to capture multispectral image data including one or more images of biological tissue (e.g., surfaces), and may be specifically configured to capture imagery within a surgical environment. For some embodiments, different biological tissues may be visible when illuminated by different wavelengths of a multispectral light source. The wavelength setting for the multispectral light source may be determined based upon a first wavelength setting associated with a first set of multispectral image data and a second wavelength setting associated with a second set of multispectral image data.

8 Claims, 6 Drawing Sheets

(51) Int. Cl.
*A61B 90/00* (2016.01)
*A61B 1/04* (2006.01)

(56) References Cited

U.S. PATENT DOCUMENTS

| | | | | |
|---|---|---|---|---|
| 5,029,016 | A * | 7/1991 | Hiyama | G11B 27/105 |
| | | | | 358/448 |
| 5,255,087 | A * | 10/1993 | Nakamura | A61B 1/0638 |
| | | | | 348/E5.038 |
| 5,583,566 | A * | 12/1996 | Kanno | G11B 27/105 |
| | | | | 386/E9.041 |
| 5,732,150 | A * | 3/1998 | Zhou | G01N 1/312 |
| | | | | 382/164 |
| 6,120,435 | A * | 9/2000 | Eino | A61B 1/00042 |
| | | | | 348/E5.042 |
| 2003/0158470 | A1* | 8/2003 | Wolters | A61B 5/0084 |
| | | | | 600/317 |
| 2003/0159141 | A1* | 8/2003 | Zacharias | H04N 5/445 |
| | | | | 348/E5.093 |
| 2004/0239760 | A1* | 12/2004 | Shoji | A61B 1/0005 |
| | | | | 348/E7.087 |
| 2006/0109558 | A1* | 5/2006 | Nishioka | B82Y 20/00 |
| | | | | 359/642 |
| 2007/0088192 | A1* | 4/2007 | Takeuchi | A61B 1/000094 |
| | | | | 600/101 |
| 2007/0185378 | A1* | 8/2007 | Higuchi | A61B 1/0002 |
| | | | | 600/109 |
| 2008/0079803 | A1* | 4/2008 | Sekiguchi | A61B 1/0005 |
| | | | | 348/45 |
| 2010/0171821 | A1* | 7/2010 | Jacobsen | A61B 1/0638 |
| | | | | 600/476 |
| 2010/0188492 | A1* | 7/2010 | Jacobsen | A61B 1/00188 |
| | | | | 348/E7.085 |
| 2014/0275760 | A1* | 9/2014 | Lee | A61B 34/37 |
| | | | | 600/102 |
| 2014/0375781 | A1* | 12/2014 | Ono | A61B 1/05 |
| | | | | 348/61 |
| 2015/0046818 | A1* | 2/2015 | Wade | A61B 1/000094 |
| | | | | 715/719 |
| 2015/0185421 | A1* | 7/2015 | Leavesley | G02B 6/4296 |
| | | | | 250/459.1 |
| 2016/0003613 | A1* | 1/2016 | Atiya | G01B 11/25 |
| | | | | 356/612 |
| 2016/0381278 | A1* | 12/2016 | Kang | A61B 1/00018 |
| | | | | 348/68 |
| 2017/0086938 | A1* | 3/2017 | Mak | A61B 90/30 |
| 2017/0163875 | A1* | 6/2017 | Takao | H04N 13/218 |
| 2017/0243079 | A1* | 8/2017 | Hiriyannaiah | G02B 27/288 |
| 2018/0092521 | A1* | 4/2018 | Nolan | A61B 1/000094 |

* cited by examiner

CONVENTIONAL

SYSTEMS AND METHODS FOR CLOSED-LOOP SURGICAL IMAGING OPTIMIZATION

PRIORITY CLAIMS

This application is a continuation of U.S. patent application Ser. No. 15/729,130, filed Oct. 10, 2017, which claims the benefit of U.S. Provisional Patent Application Ser. No. 62/406,216, filed on Oct. 10, 2016, the contents of which are incorporated herein by reference.

TECHNICAL FIELD

The technology disclosed herein relates to imaging tools and, in particular, some embodiments relate to systems and methods for closed-loop image optimization in a medical environment, such as a surgical environment.

DESCRIPTION OF THE RELATED ART

Minimally invasive medical procedures have been increasing in popularity and have become commonplace in-patient care. For instance, endoscopes and other types of medical imaging devices are indispensable tools in patient care, especially in in-patient and out-patient surgical environments. Advantages of using endoscopes include the ability to avoid large incisions and the ability to image a tissue such as, for example, biological tissue within a body cavity and biological tissue that is accessed through a small incision formed by a minimally invasive surgical device.

Endoscopes are traditionally long, thin optical instruments that may be introduced into a subject's body to illuminate and image body cavities, organs or other tissue. Endoscopes traditionally include a long, thin set of tubes that illuminate the subject tissue or cavity using illumination fibers. Many endoscopes also include one or more lenses that focus images of the illuminated body cavity onto an eyepiece and/or imaging lens. Still or video cameras may be used to capture the images returned by the endoscope.

Due to their small size (e.g., they may be as small as a few millimeters in diameter), endoscopes enable surgeries to be performed in a manner that is less intrusive and often safer for patients. For, example endoscopes may be introduced through small incisions as well as through body cavities such as, for example, the nose and throat. While this brings many benefits to patients, it presents a number of challenges for the surgeon who must work within a very confined surgical compartment. In particular, surgeons must deal with poor visibility, limited lighting, and a narrow viewing angle. Because of their size, conventional endoscopes (and the like) tend to have limited imaging resolution, often fail to provide more than one perspective of biological tissue, and due to visible lighting constraints, often fail to show differences in biological tissue (healthy vs. diseased) and/or sources of bleeding.

Figure 1:
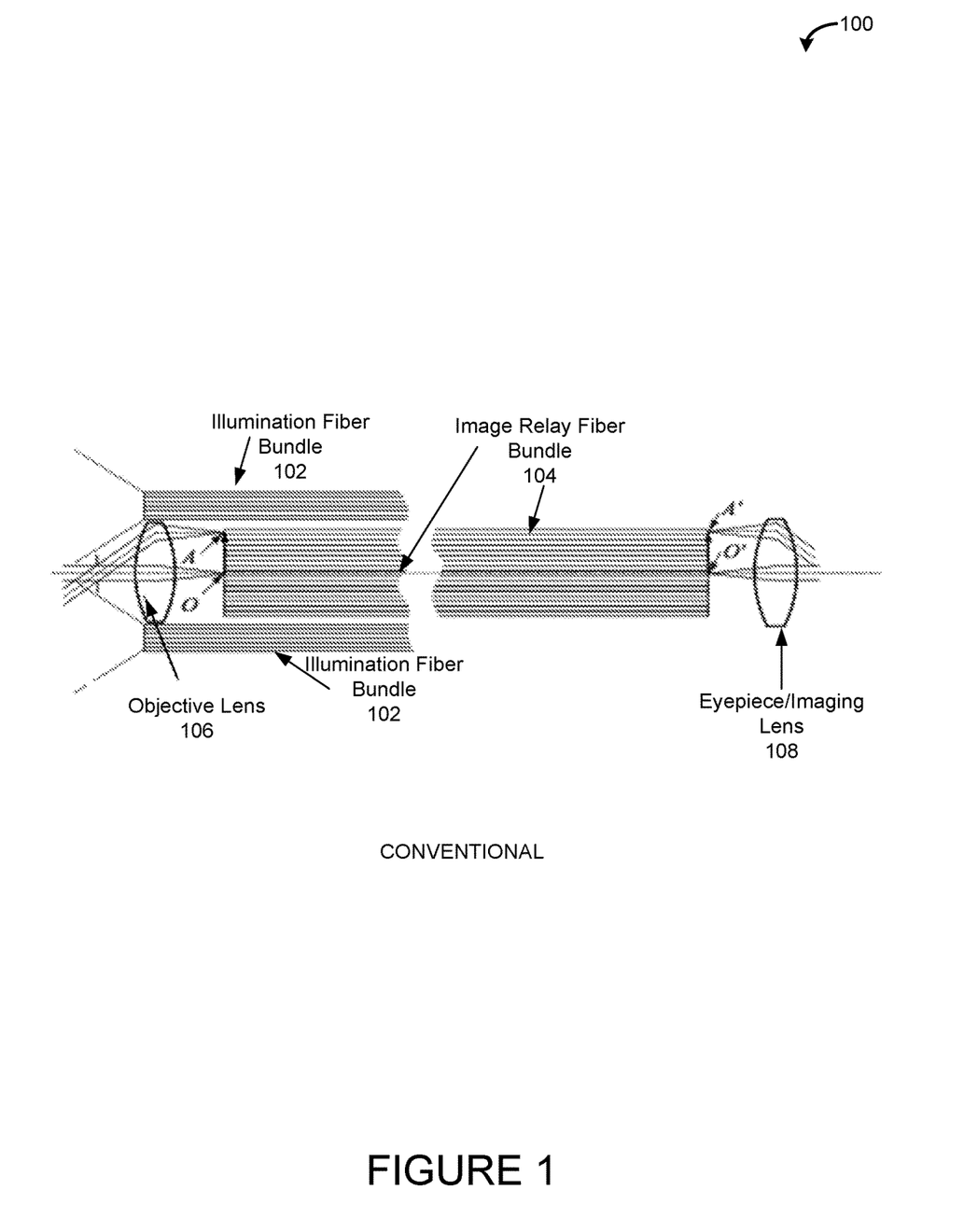
FIG. 1 is a diagram illustrating a portion of a conventional endoscope medical device.

FIG. 1 is a diagram illustrating one example of a portion of a conventional endoscope medical device 100. The conventional endoscope 100 includes illumination fiber bundles 102, image relay fiber bundles 104, an objective lens 106, and an eyepiece/imaging lens 108.

The illumination fiber bundles 102 may include one or more optical cables or fibers configured to transport light from a light source (not shown) at the proximal end to illuminate biological tissue. The illumination fiber bundles 102 may each include, for instance, up to 50,000 separate optical fibers, each configured to provide light to the biological tissue. The objective lens 106 may receive images as reflections of light from the biological tissue that has been illuminated by the illumination fiber bundles 102. Objective lens 106 focuses the image onto the distal end of the fibers of image relay fiber bundle 104 and the focused image is coupled into the fibers of the image relay fiber bundle 104.

The image relay fiber bundles 104 may include one or more optical cables or fibers that transmit images of the biological tissue to the eyepiece/imaging lens 108. The image relay fiber bundles 104 may each include, for example, up to 50,000 separate optical fibers, each configured to relay imagery of biological tissue from the objective lens 106 to the eyepiece/imaging lens 108. The eyepiece/imaging lens 108 may display the imagery of the biological tissue to a camera which may display it on a surgical monitor (not shown in FIG. 1). The eyepiece/imaging lens 108 may focus the reflections so that a user can view the reflections. In alternative conventional endoscopes, a camera or image sensor (not shown) may either be coupled to or take the place of the eyepiece/imaging lens 108. The camera may capture medical images (still medical images and/or a medical video) of the reflections on a medical image display system (not shown) that records the images.

Increasingly, conventional endoscopes, such as the conventional endoscope 100 are being replaced by video endoscopes that transmit surgical imagery to a display monitor for easier viewing by the surgeon and other members of the medical team. Video endoscopes are similar to traditional endoscopes, except that they rely on a sensor, such as a Charge Coupled Device (CCD) that is mounted toward the distal end of the endoscope. Video endoscopes may also include supporting electronics and/or a camera head that allow the surgeon to control the view. Video endoscopes offer many advantages over traditional endoscopes, including a larger view, image enhancement for improved clarity, and video recording capability. However, lack of image optimization and clear visibility due to lighting constraints of ordinary light sources remain as limiting factors in terms of image clarity, detail, and depth when viewing biological tissue, cells, etc.

SUMMARY OF THE INVENTION

Various embodiments of the systems and methods described herein may relate to closed-loop imaging in a medical environment. Particularly, various embodiments may include a surgical camera, such as an endoscopic camera, that includes one or more image sensors. The sensor may be configured to capture static images or video, may be configured to capture imagery of organs, body cavities or other biological tissue (i.e., a selected subject), and may be specifically configured to capture images of the selected subject within a surgical environment. The captured images and/or video may be referred to as multispectral image data. A key aspect of the sensor is that it is sensitive to the various wavelengths of the multispectral light source.

The array of image sensors may be disposed at or near the head of the surgical camera. The array of image sensors may utilize a plurality of image sensors, such as charge-coupled devices (CCDs). With use of the image sensors, embodiments may be configured to obviate the need to relay an image from an objective lens. This may be accomplished, for example, by configuring an objective lens to transmit an image (of the biological tissue) directly to sensing elements in the array of image sensors. For some embodiments, the surgical camera may include an imaging sensor, an objective lens, and illumination optics. The illumination optics may be included within the surgical camera, coupled to the surgical camera, and/or may be separate from the surgical camera. It will be appreciated that the array of image sensors may comprise, for example, CCDs, non-CCD image sensors such as Complementary Metal-Oxide-Semiconductor (CMOS) sensors, electron multiplication CCD or EMCCD image sensors, or some combination of sensor types. The arrangement of image sensors in the array may vary between embodiments. The image sensors may be arranged, for example, as a plane, as a sphere, as a square, as a rectangle, as a circle, or as a triangle.

Various embodiments may include an image processing system configured to process and optimize multispectral image data in real-time using specific image processing algorithms. In various embodiments, algorithms or other processing techniques may be used to determine a proper wavelength setting for a multispectral light source to illuminate an area of interest (AOI). Boundaries between normal tissue and diseased tissue may not be visible under ordinary light. This may be cumbersome for a medical professional and/or practitioner (e.g., a surgeon) performing a medical procedure, as it may be beneficial to see as much as possible during the procedure, including greater detail of tissues, cells, bleeding, etc. For example, it would be beneficial for the surgeon and/or medical team to see boundaries between healthy tissue and diseased tissue with greater clarity. Multispectral imaging may use a portion of the electromagnetic spectrum to illuminate the AOI during surgery. The multispectral light source may illuminate the AOI at varying wavelength settings or varying sequences of wavelength settings. Illuminating the AOI at the proper wavelength setting for a particular procedure and/or AOI may enable a wider range of visibility of the AOI and reveal information and details about the AOI that would otherwise be undetectable to the human eye in ordinary light.

Multispectral image data may be associated with a particular wavelength setting of the multispectral light source such that the AOI may be illuminated by the multispectral light source under the particular wavelength setting. The multispectral image data may be processed to determine the visibility of one or more images of the multispectral image data. In some embodiments, determining the visibility of the images may include determining a number of visible edges of the one or more images using an edge detection algorithm.

This process may be repeated and/or looped until a particular wavelength setting is determined to be an ideal and/or proper wavelength setting for the particular procedure and/or AOI. For example, a first number of visible edges may be determined for a first image associated with a first wavelength setting, a second number of visible edges may be determined for a second image associated with a second wavelength setting, a third number of visible edges may be determined for a third image associated with a third wavelength setting, a fourth number of visible edges may be determined for a fourth image associated with a fourth wavelength setting, and so on. The number of edges for the different images associated with each of wavelength settings may be compared to one another to determine the proper (e.g., ideal or correct) wavelength setting for the procedure and/or AOI. The image associated with the wavelength setting which may include the largest number of visible edges (denoting more tissue and/or object identification and more clarity than the other images associated with the other wavelength settings) may be selected as the proper wavelength setting for the procedure and/or AOI. The multispectral light source may be adjusted to illuminate the AOI during the procedure with light produced at the proper wavelength setting.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

The figures are not intended to be exhaustive or to limit embodiments described herein to the precise form disclosed. It should be understood that any embodiments described herein may be practiced with modification and alteration, and that the disclosed technology be limited only by the claims and the equivalents thereof.

DETAILED DESCRIPTION OF THE PREFERRED EMBODIMENT

Systems and methods disclosed herein provide an imaging system such as an endoscopic imaging system for a variety of applications. Embodiments of the systems and methods disclosed herein may be configured to utilize a plurality of image sensors as an array of image sensors to capture multispectral image data for display or recording. The array of image sensors may be included within an endoscope in some embodiments. In various embodiments, algorithms or other processing techniques may be used to determine a proper wavelength setting for a multispectral light source to illuminate an area of interest (AOI).

Visual acuity of the subject tissue or other AOI may be affected by the wavelength of light used to illuminate the work area. For example, boundaries between normal tissue and diseased tissue may not be visible (or may be difficult to discern) under ordinary light or under light of certain wavelengths. These difficulties may vary based on the tissue types being imaged or based on other properties of the AOI. This may lead to concerns for a medical professional or practitioner (e.g., a surgeon) performing a medical procedure, as it is typically beneficial to see certain or specific types of details during the procedure, including greater detail of tissues, cells, bleeding, etc. For example, it would be beneficial for the surgeon and/or medical team to better discern boundaries between healthy tissue and diseased tissue with greater clarity, or to otherwise have improved acuity during procedures.

By way of more specific examples, some cancerous tissues may be visible under a wavelength range of 400 nm to 650 nm while oral cancer cells may be visible under a wavelength range 400 nm to 800 nm. In yet another example, breast tumors may be visible under a wavelength range of 580 nm to 745 nm. Illuminating the AOI at the proper wavelength setting for a particular procedure and/or AOI may enable a wider range of visibility of the AOI and reveal information and details about the AOI that would otherwise be undetectable to the human eye or image sensor in ordinary light.

Accordingly, in various embodiments, multispectral imaging may use a portion of the electromagnetic spectrum to illuminate the AOI during surgery. In some embodiments, the multispectral light source may illuminate the AOI at predetermined wavelength settings, while in other embodiments, the multispectral light source may illuminate the AOI at varying wavelength settings or varying sequences of wavelength settings so that appropriate wavelength or wavelengths may be at determined for the given AOI. For example, in some embodiments, the system may be configured to step or otherwise transition the multispectral light source through various wavelengths so that the best wavelength may be determined for the given procedure or AOI. Determination of which wavelength, wavelength range, or combination of wavelengths is best for a given procedure or AOI may be made by the medical professional performing or involved with the procedure, or it may be made automatically based on image processing algorithms as further discussed below.

In various embodiments, an array of image sensors may be used to capture multispectral image data from a surgical camera. The surgical camera may include a surgical camera mounted on an endoscope. The multispectral image data may be associated with a particular wavelength setting of the multispectral light source such that the AOI may be illuminated by the multispectral light source under the particular wavelength setting, or under a plurality of different wavelength settings.

The multispectral image data may be processed to determine the visibility of one or more images of the multispectral image data. In some embodiments, determining the visibility of the images may include determining a number of detectable edges of an identified feature (e.g., a tumor, etc.) in the one or more images using an edge detection algorithm.

This edge detection process may be repeated or looped until a particular wavelength setting is determined to be an ideal or proper wavelength setting for the particular procedure and/or AOI. For example, a first number of visible edges may be determined for a first image associated with a first wavelength setting, a second number of visible edges may be determined for a second image of the AOI associated with a second wavelength setting, a third number of visible edges may be determined for a third image of the AOI associated with a third wavelength setting, a fourth number of visible edges may be determined for a fourth image associated with a fourth wavelength setting, and so on. The number of edges for the different images associated with each of the wavelength settings may be compared to one another to determine the proper (e.g., ideal or correct) wavelength setting for the procedure and/or AOI. The image associated with the wavelength setting that may include the largest number of visible edges or otherwise based on a function of the number of visible edges, or criteria related to image analysis such as signal to noise ratio (denoting a better object identification and more clarity than the other images associated with the other wavelength settings) may be selected as the proper wavelength setting for the procedure and/or AOI. The multispectral light source may be adjusted to illuminate the AOI during the procedure with light produced at the proper wavelength setting.

In some embodiments, specific modes for particular procedures or types of AOIs may be predefined. These modes may include defined wavelengths, wavelength ranges, combinations of wavelengths, and/or intensities that are known empirically to work well for their corresponding procedures and/or AOIs (e.g. such as through prior determination using the edge-detection process described above). The system may be configured such that these modes may be selected for the procedure or AOI either manually by the medical professional or automatically when the endoscope is set up for the particular operation. The particular procedure and/or AOI may be received by user input such that these predefined settings and/or modes associated with the particular procedure and/or AOI may be set for the multispectral light source.

Wavelength selection may occur after the endoscope has been placed and/or inserted for the procedure and may occur in real-time. Wavelength selection may be made prior to initiation of the procedure, or it may be made or updated part way through the procedure. Once the proper wavelength setting has been selected and adjusted via the multispectral light source, the surgeon may initiate or continue the procedure while viewing the images and/or stream of images (e.g., multispectral image data) which have been optimized using the closed-loop image optimization for greater clarity of the AOI.

In some configurations, the locking mechanism may be provided such that the system does not continuously loop through wavelength settings once a wavelength selection has been made. The locking mechanism may disable the algorithm and this may be done automatically upon selection of the proper wavelength, or via a manual actuation that may be operated by the medical professional. Medical professionals may override the wavelength setting at any time before, during, or after the procedure, and the system may provide the ability for the medical professional to restart the automated procedure or manually adjust the wavelength as desired. As with conventional endoscopic procedures, the multispectral image data may be stored for later retrieval to review in non-real time. Wavelength setting data (including, for example, the wavelength, wavelength range, combination of wavelengths, and intensity data) may also be saved (e.g., as metadata) along with the images so that this data may later be reviewed.

Determining the visibility of one or more images of the multispectral image data may include determining visibility of the one or more images based upon a color algorithm and/or a color edge algorithm. In this manner, the wavelength selection algorithm may be configured to search for colors. Images may be produced with one or more colors and/or variations in the images may be highlighted in one or more colors.

Figure 2:
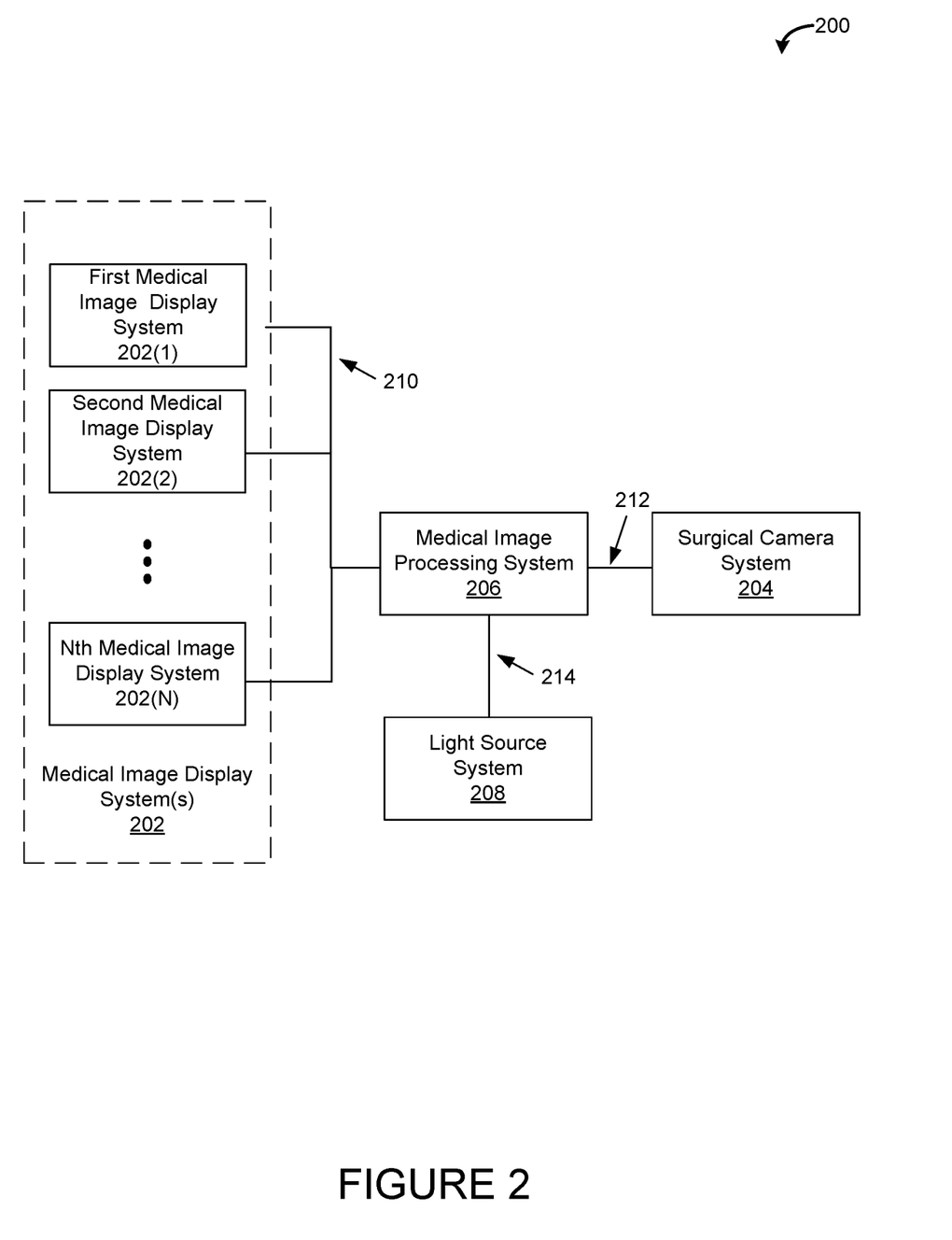
FIG. 2 is a diagram illustrating an example system-level implementation of the various embodiments of the technology disclosed herein.

Before describing the image processing and image capture technology in detail, it may be useful to describe an example application with which embodiments of the image processing and capture technology disclosed herein may be implemented. FIG. 2 is a diagram illustrating an example medical software tool 200. This example medical software tool 200 may include one or more medical image display systems 202, a surgical camera system 204, a medical image processing system 206, and a light source system 208.

In operation, images of biological tissue, a body cavity, or other samples may be captured by surgical camera system 204. Surgical camera system 204 may include, for example, an endoscope or other device configured to capture medical images of biological tissue, an organ, a body cavity, or other samples. The captured images, whether still or motion picture images, may be transferred by a wired or wireless communication link 212 to medical image processing system 206 for desired image processing. Medical image processing system 206 may perform any other image processing as desired, such as, determining a number of edges within the images, determining a proper wavelength setting for image optimization, and so on.

The images may then be provided to one or more medical image display systems 202 by a communication or datalink 210. Although medical image processing system 206 and surgical camera system 204 may be communicatively coupled to one another using a separate communication link 212 as shown, in other embodiments, they may communicate using the same communication link or bus 210 (not illustrated).

Medical image display systems 202 may include one or more display devices configured to display images captured by medical software tool 200. These displays may include, for example, a plasma display, a Liquid Crystal Display (LCD), a Light Emitting Diode (LED) display, or any display suitable for rendering images for viewing by the health care practitioners utilizing medical software tool 200. Though multiple medical image display systems 202 are shown in FIG. 2, any number of medical image display systems 202 may be provided. In some embodiments, a single medical image display system 202 may be provided.

In some embodiments, the images displayed by medical image display systems 202 may include still or video images of the biological tissue, organ, body cavity, or other samples captured by the endoscope. In some embodiments, these may be referred to as medical images. These images may be captured using a camera (such as, for example, surgical camera system 204) or other image capture device.

The proper wavelength setting may be transmitted from medical image processing system 206 to light source system 208. Light source system 208 may adjust the multispectral light source emitted during the surgery in real-time to the proper wavelength setting. One or more images may be captured of the AOI using the proper wavelength setting by surgical camera system 204 and transmitted to medical image processing system 206. The images may be transmitted to medical image display system 202. Medical image processing system 206 may repeat the process and perform image processing such as, for example, determining wavelength settings associated with the images, determining a number of edges within the images, determining a new proper wavelength setting for image optimization, and so on. The new proper wavelength setting may once again be determined and transmitted from medical image processing system 206 to light source system 208. While medical image processing system 206 may be communicatively coupled to light source system 208 using a separate communication link 214 as shown, in other embodiments, they may communicate using the same communication link or bus 210 (not illustrated). Light source system 208 may adjust the multispectral light source emitted during the surgery in real-time to the proper wavelength setting. One or more images may be captured of the AOI using the proper wavelength setting by surgical camera system 204. The images may be transmitted to medical image processing system 206. This process may be repeated in a closed-loop fashion for image optimization.

Having thus described an example implementation of the technology disclosed herein, a more detailed description of various aspects of this technology is now provided.

Figure 3:
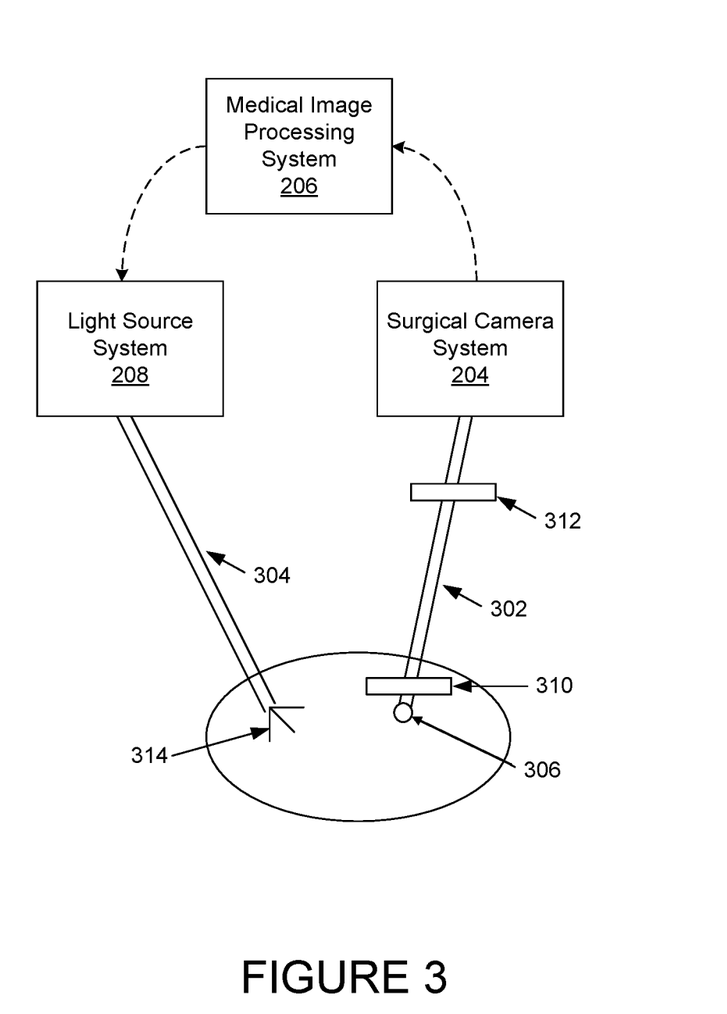
FIG. 3 is a diagram illustrating a surgical camera and a multispectral light source in accordance with one embodiment of the technology described herein.

FIG. 3 is a diagram illustrating an example closed-loop image optimization process including an endoscopic image capture device and a fiber optic cable in accordance with one embodiment of the technology disclosed herein. Particularly, the example illustrated in FIG. 3 depicts an example implementation of an insertion tube of an endoscopic camera and a fiber optic cable providing light to an AOI. In various embodiments, endoscopic image capture device 302 may be provided to implement surgical camera system 204 and fiber optic cable 304 may be provided to implement medical light source system 208. Endoscopic image capture device 302 may include lens 306 and one or more image sensors 310, 312 (e.g., an array of image sensors). One or more image sensors 310, 312 may be configured to capture multispectral image data. One or more image sensors 310, 312 may be located in different locations of endoscopic image capture device 302. For example, image sensor 310 may be located at a distal (or internal) end of the endoscopic image capture device 302, while image sensor 312 may be located at a proximal (or external) end of the endoscopic image capture device 302. Alternatively, all of one or more image sensors 310, 312 included within the array of image sensors may be located external to a human cavity or may be located within the human cavity. Multispectral image data may include one or more images captured by the array of image sensors (e.g., one or more of image sensors 310, 312).

Fiber optic cable 304 may include a multispectral light source and/or illumination fibers (not shown). While fiber optic cable 304 is shown to be separate from endoscopic image capture device 302, fiber optic cable 304 may be included within endoscopic image capture device 302 or coupled to endoscopic image capture device 302. The multispectral light source may be included within the human cavity for illumination of the AOI. The multispectral light source may be configured to produce light at different and/or varying wavelength settings, varying sequences of wavelength settings, varying combinations of wavelengths (whether or not adjacent in the spectrum), and varying intensities of wavelengths. The multispectral light source and/or illumination fibers of fiber optic cable 304 may include optical fibers that provide illumination 314 to the AOI.

Lens 306 may transmit images from the AOI to one or more image sensors 310, 312. In this case, the images are a result of light from illumination 314 being reflected off the AOI. Lens 306 may be configured to transmit or project the image to image sensors 310, 312. While only one lens is shown in FIG. 3, this is for exemplary purposes only and is not meant to be a limitation of this disclosure, as endoscopic image capture device 302 may include more than one lens 306. In yet other embodiments, other optical structures may be used to transmit the images from a distal end of endoscopic image capture device 302 to image sensors 310, 312. For example, embodiments may be implemented using optical fibers or a fiber bundle in place of or in addition to lens 306.

One or more of image sensors 310, 312 may capture the images from the reflections of illumination 314 off the AOI and transform the optical signal into an electrical representation of the image. Once transformed into an electrical representation, this image information may be stored and processed as appropriate depending on the use or application. For example, this information may be transferred to a processing system such as medical image processing system 206 for processing and storage.

Image sensors 310, 312 may include, for example, Charge Coupled Device (CCD) sensors, CMOS image sensors, electron multiplication CCD or EMCCD image sensors, or other image sensors. In various embodiments, the image sensors may be configured as a focal plane array of image sensors. Accordingly, a plurality of image sensors may be combined adjacent one another to form a sensor array.

As illustrated in FIG. 3, image sensors 310, 312 may comprise an array of image sensors. The array of image sensors may be configured to capture multispectral image data via reflections from the AOI. Multispectral image data may include image data captured at varying frequencies across the electromagnetic spectrum. Wavelengths may be separated by filters or by the use of instruments that are sensitive to particular wavelengths, including light from frequencies beyond the visible light range, such as infrared. Multispectral imaging may allow for extraction of additional information the human eye may fail to capture with its receptors for red, green and blue. For example, a specific wavelength may enable assessment of a wide range of tissue and blood chromophores such as oxy-hemoglobin, deoxy-hemoglobin, and bilirubin. Other wavelengths in the near infrared spectrum compared to those in the visible light spectrum may provide added depth discrimination in images.

Referring again to the example environment of FIG. 2, medical image processing system 206 may include a first input configured to receive, from surgical camera system 204, a first set of multispectral image data associated with a first wavelength setting of the multispectral light source 208. The first wavelength setting may be automatically predefined via medical imaging processing system 206, light source system 208, and/or may be manually entered by a user of medical software tool 200 via a user interface, not shown. The user interface may include at least one of a keyboard, a touch-screen display, a pointing device or other suitable user interface device.

It may be known that specific tissue types, body parts, and/or diseases may not be readily visible to the human eye under conventional 'white' light or other like broad-spectrum illumination, but may be visible when illuminated under a particular wavelength. For example, some cancerous tissues may be visible under a wavelength range of 400 nm to 650 nm while oral cancer cells may be visible under a wavelength range 400 nm to 800 nm. In yet another example, breast tumors may be visible under a wavelength range of 580 nm to 745 nm.

In the instances where a wavelength range may be known for a particular procedure and or AOI (a particular type of procedure may be preconfigured via a user input prior to the procedure), medical image processing system 206, light source system 208, and/or user of medical imaging system 100 may set and/or define a wavelength setting to be within the wavelength parameters known for that particular procedure to begin the process. If a wavelength setting is not known for the particular procedure, or if the procedure is exploratory in nature, the first wavelength setting may be preset to a wavelength within ordinary lighting visible by the human eye. This might include, for example, broader spectrum of illumination. Fiber optic cable 304 may illuminate the AOI via illumination 314 with the first wavelength setting. As discussed above, one or more of image sensors 310, 312 of the array of image sensors may capture the multispectral image data from the reflections of illumination 314 off the AOI (illumination 314 being a result of the first wavelength setting). Medical image processing system 206 may receive, from surgical camera system 204, the first set of multispectral image data as a result from the reflections of illumination 314 based upon the first wavelength setting. The multispectral image data may be stored and/or processed by medical image processing system 206.

Medical image processing system 206 may include a second input configured to receive, from surgical camera system 204, a second set of multispectral image data associated with a second wavelength setting of the multispectral light source (e.g., fiber optic cable 304). The second wavelength setting may be different than the first wavelength setting. Light source system 208 may automatically adjust the first wavelength setting to the second wavelength setting once the first set of multispectral image data has been transmitted to surgical camera system 204 and/or medical image processing system 206. A user of medical software tool 200 may manually adjust the first wavelength setting to the second wavelength setting via the user interface (not shown). Fiber optic cable 304 may illuminate the AOI via illumination 314 with the second wavelength setting. As discussed above, one or more of image sensors 310, 312 of the array of image sensors may capture the multispectral image data from the reflections of illumination 314 off the AOI (illumination 314 being a result of the first wavelength setting). Medical image processing system 206 may receive, from surgical camera system 204, the second set of multispectral image data as a result from the reflections of illumination 314 based upon the second wavelength setting. The multispectral image data may be stored and/or processed by medical image processing system 206.

Medical image processing system 206 may be configured to select a proper wavelength setting for the multispectral light source based upon the first set of multispectral image data and the second set of multispectral image data. Medical image processing system 206 may compare the first set of multispectral image data to the second set of multispectral image data to determine which of the first set of multispectral image data and/or the second set of multispectral image data may be the proper (or more appropriate) wavelength setting out of the given sets of multispectral image data. The proper wavelength setting may be selected based upon an edge detection algorithm. The edge detection algorithm may be used to determine a number of visible edges of the multispectral image data.

Edge detection may include methods that may identify points or boundaries between features in an image at which the image brightness or color may change sharply or has discontinuities. Points at which image brightness or color changes sharply may be organized into a set of curved line segments called "edges". Discontinuities in image brightness may correspond to discontinuities in depth, surface orientation, variations in physical properties, and/or variations in illuminations. Edge detection may provide a set of curves that indicate boundaries of objects, the boundaries of surface markings, and/or curves that correspond to discontinuities in surface orientation.

Medical image processing system 206 may detect the edges and determine a first number of visible edges of the first set of multispectral image data via the edge detection algorithm. Due to illuminating the AOI with different wavelengths, different edges may be detected with different wavelengths, or edges may simply be more or less detectable at different wavelengths. As described above multispectral image data may include multiple images. Medical image processing system 206 may determine a first number of visible edges for each of the images included within the first set of multispectral image data or may determine a first number of visible edges for a portion of the one or more images included within the first set of multispectral image data. The first number of visible edges may be determined for a single image of the first set of multispectral image data. If a number of visible edges is determined for more than one image of the first set of multispectral image data, the number of visible edges may be added together and/or averaged to obtain a result for the first set of multispectral image data.

Medical image processing system 206 may determine a second number of visible edges of the second set of multispectral image data via the edge detection algorithm. Medical image processing system 206 may determine a second number of visible edges for each of the one or more images included within the second set of multispectral image data or may determine a second number of visible edges for a portion of the one or more images included within the second set of multispectral image data. The second number of visible edges may be determined for a single image of the second set of multispectral image data, or for multiple images. If a number of visible edges is determined for more than one image of the second set of multispectral image data, the number of visible edges may be added together and/or averaged.

Medical image processing system 206 may select the proper wavelength setting based upon the first set of multispectral image data and the second set of multispectral image data. As described above, the first set of multispectral image data may be retrieved when the multispectral light source is set to the first wavelength setting. The second set of multispectral image data may be retrieved when the multispectral light source is set to the second wavelength setting. The results of the edge detection process may be compared to determine which wavelength setting yields the better result. For example, the first wavelength setting may be selected as the proper wavelength setting if the first number of visible edges (e.g., the first number of visible edges for the first set of multispectral image data) is greater than the second number of visible edges (e.g., the second number of visible edges for the second set of multispectral image data).

Alternatively, the second wavelength setting may be selected as the proper wavelength setting if the second number of visible edges is greater than the first number of visible edges. If the first number of visible edges and the second number of visible edges are equivalent (preferably based upon an equivalent number of images), either of first wavelength setting or second wavelength setting may be selected as the proper wavelength setting.

Although the above process was described with two sets of multispectral image data, one of ordinary skill in the after art reading this description will understand that the process may be carried out using more than two sets of multispectral image data. In such embodiments, the comparison may be made after each set of image data is collected after the first set, to compare the results of a current setting with the previous setting to determine which wavelength setting yields the better result. In other embodiments, the data may be gathered for all of the settings used, and the comparison made after the information has been gathered for each setting. As these examples illustrate, there are number of approaches to gathering the edge detection results for multiple wavelength settings and comparing the results to choose the wavelength setting that provides the best results.

The proper wavelength setting may also be selected based upon a color detection algorithm and/or a color edge detection algorithm. Color detection algorithms may search for one or more colors. For example, medical image processing system 206 may receive multispectral image data including one or more colors, subtle variations of content of the multispectral image data (e.g., tissues, cells, bleeding, etc.) may be highlighted in one or more colors, etc. Further, color edge detection algorithms may determine a number of visible edges using one or more colors. Accordingly, the detection algorithm may be configured to look for the numbers of different colors (colors may be defined by ranges) in an image, the sharpness of transition from one color to the next, the number of edges or definition of edges between the colors, and so on. Similar techniques may be used for intensities such as the number of different intensity ranges in an image, the sharpness of transition from one region of intensity to another region of a different intensity, the number of edges or the definition of edges between intensity regions, and so on.

Medical image processing system 206 may include a first output configured to provide instructions to light source system 208 to adjust the multispectral light source to produce light at the identified preferred wavelength setting. Light source system 208 may include an input coupled to the output of medical image processing system 206 to receive the instructions from medical image processing system 206. Light source system 208 may receive the instructions from medical image processing system 206 in real-time. Light source system 206 and/or the multispectral light source may be adjusted in real-time to produce light at the proper wavelength setting based upon the received instructions. For example, wavelength settings may adjust automatically prior to the surgeon beginning the rest of the procedure/surgery or during an ongoing procedure without user input therefore not disrupting any medical professionals from the ongoing procedure itself.

This process may be repeated until image optimization has been automatically obtained and/or determined for the particular procedure based upon the number of visible edges within images obtained using a particular wavelength setting of the multispectral light source. For example, a third number of visible edges of a third set of multispectral image data may be determined via the edge detection algorithm. The third set of multispectral image data may be received by medical image processing system 206 and the third number of visible edges may be determined for the third set of multispectral image data in a similar manner as described above. The third number of visible edges may be compared to a number of visible edges for multispectral image data associated with the proper wavelength setting (in this example, either the first wavelength setting or the second wavelength setting). Medical image processing system 206 may select the third wavelength setting as a new proper wavelength setting if the third number of visible edges is greater than the number of visible edges of the multispectral image data associated with the proper wavelength. The new proper wavelength setting may include a second proper wavelength setting that is the same wavelength setting as the proper wavelength setting or a different wavelength setting from the proper wavelength setting. Medical image processing system 206 may provide instructions to light source system 208 to adjust the multispectral light source to produce light at the new proper wavelength setting. Light source system 208 may receive the instructions from medical image processing system 206 in real-time. Light source system 206 and/or the multispectral light source may be adjusted in real-time to produce light at the new proper wavelength setting based upon the received instructions.

As noted above, in another embodiment, an initial comparison may be done after all of the multispectral data sets have been received, such that a proper wavelength setting is selected once and does not continuously update based upon a previously selected proper wavelength setting. For example, upon determining the first number of visible edges, the second number of visible edges, and the third number of visible edges, the multispectral image data associated with the wavelength setting with the largest number of visible edges out of the three multispectral image data sets may be selected as the proper wavelength setting.

While the process may be automated, the system may also be configured to allow a user to select, via a user interface, the proper wavelength setting after reviewing the outputs of the various multispectral image data sets and/or the number of visible edges associated with the various multispectral image data sets.

Upon the multispectral light source being adjusted to produce light at the proper wavelength setting (whether initial proper wavelength setting or a new proper wavelength setting), a locking mechanism may be provided such that the closed-loop imaging process does not continue to loop through different wavelengths in order to generate more multispectral image data. This locking mechanism may disable the algorithm and this may be done automatically upon selection of the proper wavelength so that the procedure may not be disrupted, or via a manual actuation that may be operated by the medical professional. As discussed below, the system user may manually override the proper wavelength setting or the new proper wavelength setting via the user interface.

Medical image processing system 206 may include a second output to provide the multispectral image data captured by the array of image sensors. Medical software tool 200 may include a display monitor (e.g., a display monitor, not shown, included within medical image display system 202 of FIG. 1) having an input coupled to the second output of medical image processing system 206 to display the multispectral image data captured by the array of image sensors. The clarity of the multispectral image data captured by the array of image sensors may be based upon the multispectral light source. As discussed above, diseased tissue may not be visible under visible light but may be visible under particular wavelengths. It is important for medical professionals to view the most clear and precise image as possible during a procedure to ensure that all of the diseased tissue and/or cells have been removed, to determine if there is any bleeding, to determine if there are any other areas of concern, etc.

A system user may manually override the proper wavelength setting or the new proper wavelength setting via the user interface (not shown). The manual override may be transmitted to the multispectral light source to be set to a particular setting which the user manually defined. This may occur at any point before, during, or after the procedure. The user may also retrieve previously stored images to compare to real-time multispectral image data during the procedure via the display monitor of medical image display system 202.

Figure 4:
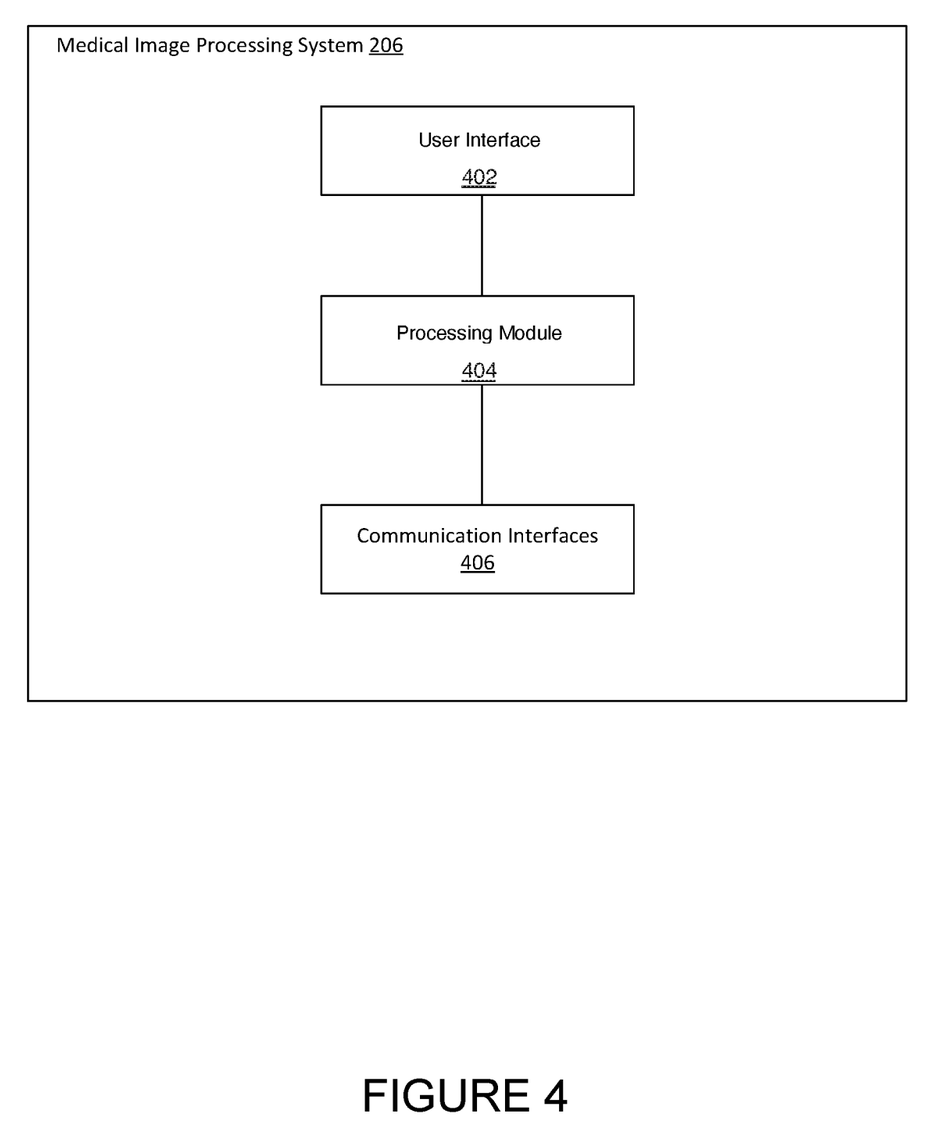
FIG. 4 is a diagram illustrating a medical image processing system in accordance with one embodiment of the technology described herein.

FIG. 4 is a diagram illustrating an example of a medical image processing system according to some embodiments. Medical image processing system 206 in this example includes one or more user interfaces 402, processing module 404, and communication interfaces 406.

User interface overlay module 402 may be configured to allow a user to control various aspects of the medical software tool 200, such as, for example, medical image display system(s) 202 and/or surgical camera system 204. User interface overlay module 402 may be configured to allow a user to perform operations such as, for example, (i) guide the distal end of medical imaging system 302 to a specified location such as a specific body cavity or a specific section of biological tissue; (ii) allow the user to control the camera system to capture images, select an AOI for viewing or capture, magnify an AOI, sample an AOI, sample different perspectives of the subject (different views, different magnifications, different angles, etc.), and so on; (iii) select for display one or more particular perspectives of biological tissue; and (iv) control the light source.

In various embodiments, the user interface overlay module 402 may include a keypad, keyboard, mouse or pointing device, touchscreen interface, or other user interface that allows a user to control the medical software tool 200 or to otherwise provide input to the medical software tool 200.

The processing module 404 may be configured to control user interface 402 and communication interfaces 406 and to otherwise perform the processing and control for medical image processing system 206. This processing may include, for example, processing images for edge detection, clarity and acuity, image enlargement or magnification, AOI selection and display, and other image processing and operational processing as further described herein. The processing module 404 may include one or more processors and associated non-transitory memory to perform these functions.

Image stream processing module 404 may include hardware, software, and/or firmware configured to compress and/or decompress image sensor data for display. In some embodiments, image stream processing module 404 may use edge detection algorithms to determine a number of visible edges within the multispectral image data and display the multispectral image data via medical image display system(s) 202.

Figure 5:
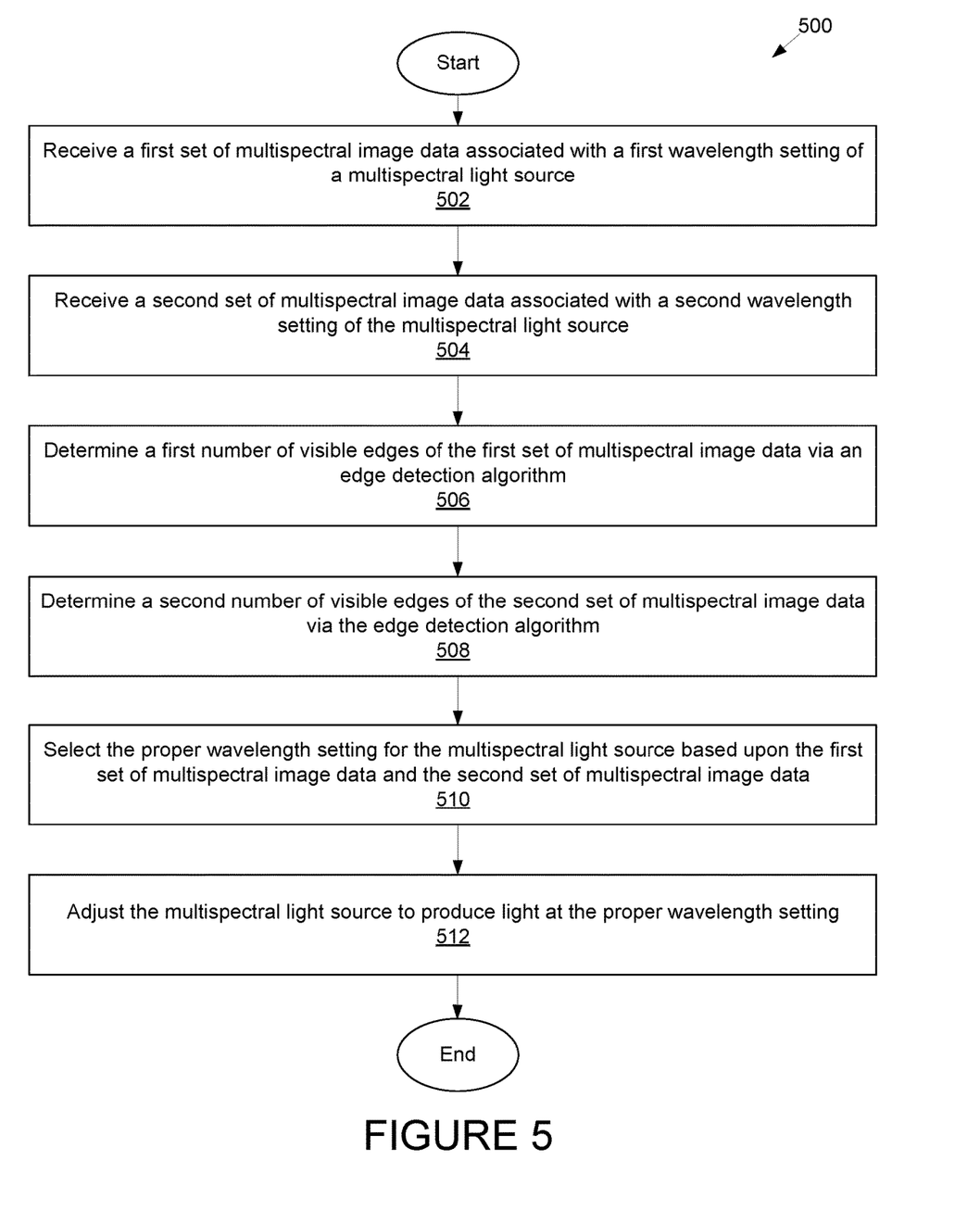
FIG. 5 is a flowchart illustrating a method for closed-loop medical imaging in accordance with one embodiment of the technology described herein.

FIG. 5 is a flowchart illustrating an example process for closed-loop image optimization, according to some embodiments. At step 502, medical image processing system 206 may receive a first set of multispectral image data associated with a first wavelength setting of a multispectral light source. At step 504, medical image processing system 206 may receive a second set of multispectral image data associated with a second wavelength setting of the multispectral light source. As discussed above, the multispectral image data may be a result of reflections off of the AOI of illuminations of a particular wavelength setting on the AOI.

At step 506, medical image processing system 206 may determine a first number of visible edges of the first set of multispectral image data via an edge detection algorithm. At step 508, medical image processing system 206 may determine a second number of visible edges of the second set of multispectral image data via the edge detection algorithm. At step 510, the number of visible edges for the different multispectral image data may be compared such that the wavelength setting associated with the multispectral image data set which may provide the highest and/or largest number of visible edges may be selected as the proper wavelength setting. At step 512, the multispectral light source may be adjusted to produce light at the proper wavelength setting. This process may include receiving more than two multispectral image data sets. For example, a third set of multispectral image data and a fourth set of multispectral image data may be received. A third number of visible edges for the third set of multispectral image data and a fourth number of visible edges for the fourth set of multispectral image data may be determined. The third number of visible edges and the fourth number of visible edges may be compared to one another, compared to the proper wavelength setting, and/or compared to the first number of visible edges and/or the second number of visible edges to determine the proper wavelength setting and/or determine a new proper wavelength setting (e.g., a second proper wavelength setting in the case where there may be more than two proper wavelength settings as this process continues looping through different wavelength settings).

As noted above, in some embodiments the systems and methods described herein may be configured to magnify or enlarge desired AOIs of the overall captured image. Magnification of images may permit a medical professional and/or practitioner, such as a surgeon, to "zoom" in on portions of images provided by the surgical camera and view greater resolution of the AOI. For some embodiments, the image processing system may permit an operator to locate the display area and size of the AOI whether in a still image, a recorded video stream or a live video image stream.

To facilitate identification of wavelength settings for future use, selected wavelength settings and/or wavelength ranges for particular procedures and/or AOIs for the procedure may be stored in memory. Accordingly, for a similar procedure in the future, the system user may select the procedure and/or AOI for the procedure. The first wavelength setting may be set to the stored wavelength setting based upon similarities of procedures and/or AOIs.

Multiple display monitors may be provided and arranged as appropriate for the environment. For example, one or more display monitors may be placed at one or more operational stations in the operating theater to allow various healthcare professionals performing various tasks to view the procedure.

Figure 6:
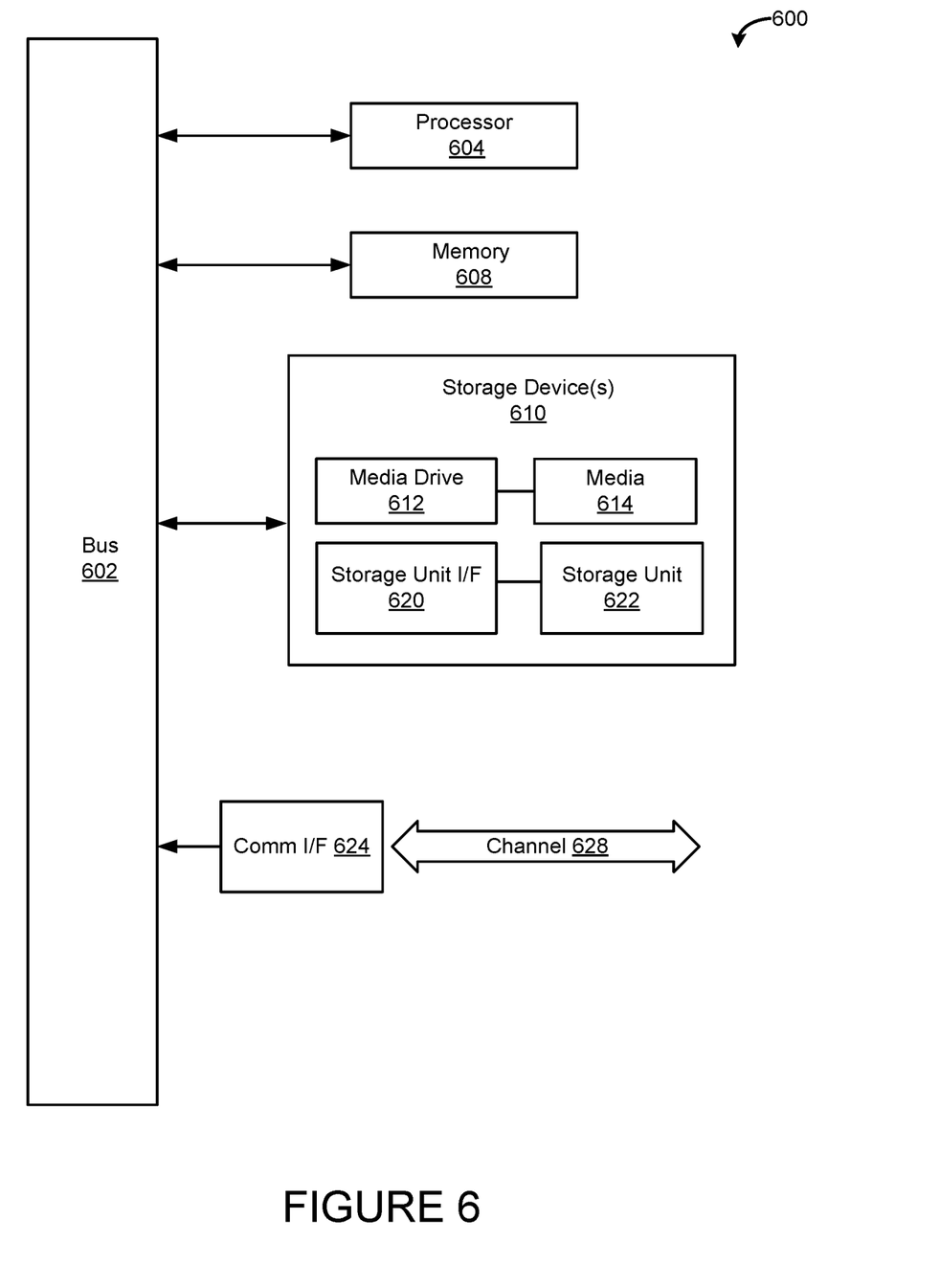
FIG. 6 illustrates an example medical device interface module that may be used in implementing various features of embodiments of the disclosed technology.

As used herein, the term module might describe a given unit of functionality that may be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the technology are implemented in whole or in part using software, in one embodiment, these software elements may be implemented to operate with a computing or processing module capable of carrying out the functionality described with respect thereto. One such example medical device interface module is shown in FIG. 6. Various embodiments are described in terms of this example medical device interface module 600. After reading this description, it will become apparent to a person skilled in the relevant art how to implement the technology using other computing modules or architectures.

In various embodiments, the Medical device interface module 600 represents, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Medical device interface module 600 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Medical device interface module 600 might include, for example, one or more processors, controllers, control modules, or other processing devices, such as a processor 604. Processor 604 might be implemented using a general-purpose or special-purpose processing engine such as, for example, a microprocessor, controller, or other control logic. In the illustrated example, processor 604 is connected to a bus 602, although any communication medium may be used to facilitate interaction with other components of medical device interface module 600 or to communicate externally.

Medical device interface module 600 might also include one or more memory modules, simply referred to herein as main memory 608. For example, preferably random access memory (RAM) or other dynamic memory might be used for storing information and instructions to be executed by processor 604. Main memory 608 might also be used for storing temporary variables or other intermediate information during execution of instructions to be executed by processor 604. medical device interface module 600 might likewise include a read only memory ("ROM") or other static storage device coupled to bus 602 for storing static information and instructions for processor 604.

The medical device interface module 600 might also include one or more various forms of information storage mechanism 610, which might include, for example, a media drive 612 and a storage unit interface 620. The media drive 612 might include a drive or other mechanism to support fixed or removable storage media 614. For example, a hard disk drive, a floppy disk drive, a magnetic tape drive, an optical disk drive, a CD or DVD drive (R or RW), or other removable or fixed media drive might be provided. Accordingly, storage media 614 might include, for example, a hard disk, a floppy disk, magnetic tape, cartridge, optical disk, a CD or DVD, or other fixed or removable medium that is read by, written to, or accessed by media drive 612. As these examples illustrate, the storage media 614 can include a computer usable storage medium having stored therein computer software or data.

In alternative embodiments, information storage mechanism 610 might include other similar instrumentalities for allowing computer programs or other instructions or data to be loaded into medical device interface module 600. Such instrumentalities might include, for example, a fixed or removable storage unit 622 and an interface 620. Examples of such storage units 622 and interfaces 620 can include a program cartridge and cartridge interface, a removable memory (for example, a flash memory or other removable memory module) and memory slot, a PCMCIA slot and card, and other fixed or removable storage units 622 and interfaces 620 that allow software and data to be transferred from the storage unit 622 to medical device interface module 600.

Medical device interface module 600 might also include a communications interface 624. Communications interface 624 might be used to allow software and data to be transferred between medical device interface module 600 and external devices. Examples of communications interface 624 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 624 might typically be carried on signals, which may be electronic, electromagnetic (which includes optical) or other signals capable of being exchanged by a given communications interface 624. These signals might be provided to communications interface 624 via a channel 628. This channel 628 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 608, storage unit 622, media 614, and channel 628. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the medical device interface module 600 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A medical image processing system for medical software tools, comprising:
    an image stream output via a surgical camera;
    a user interface comprising a keypad, keyboard, mouse or pointing device, or touchscreen interface, wherein said system stores annotations created by a user of said system to enable said user to store said annotations along with said image stream so that said annotations appear to overlay said image stream as viewed by said user;
    a medical image display system comprising, a display selected from the group consisting of a plasma display, a Liquid Crystal Display (LCD), and a Light Emitting Diode (LED) display;
    wherein said medical image display system displays surgery related images captured by a medical software tool stored historically in connection with spectroscopy assisted surgical procedures so that said system user may compare real life present time surgical conditions with prior in time historic surgical conditions for reference to enable said user to effect real time surgical decisions;
    a light source sufficient to amplify said image stream perceivable by said camera, wherein said light source is of a particular wavelength within a range of desired wavelengths and wherein said particular wavelength is modulated to scan through a continuum of wavelengths from a lower wavelength to an upper wavelength;
    wherein said scan of wavelengths is repeated until a wavelength is selected for observation of said image stream; and
    wherein said medical image processing system stores a plurality of predetermined wavelengths, ranges of wavelengths, and combinations of wavelengths and intensities that are known to be optimal for visualizing a specific organ, tissue, or area of interest (AOI) and are provided as predetermined settings based on said user's real-time AOI;
    a communication interface; and
    a processing module comprising at least one processor, a non-transitory memory, and hardware, software, or firmware configured to compress and decompress image sensor data for display, further comprising edge detection algorithms and color detection algorithms;
    wherein said algorithms determine a number of visible edges and a number of visible colors within multispectral image data that is displayed via a medical image display system.

2. The system of claim 1, wherein the user interface is further configured to retrieve previously stored images and compare the previously stored images to real-time multispectral image data during the procedure via the display monitor of the medical image display system.

3. The system of claim 1, wherein the surgical camera is an endoscope or a laparoscope.

4. The system of claim 1, wherein the processing module of the medical image processing system is further configured to receive the image stream from the surgical camera.

5. The medical image processing system of claim 1, further comprising of one or more additional processors, controllers, control modules, or other processing devices, such as a processor, wherein said system is configured to exchange data between the surgical camera system and a medical image display system by a wired or wireless communication link.

6. A method for operating medical software tools, comprising:
    receiving with a medical image processing system an image stream from a surgical camera system; the medical image processing system providing a user input device so that said user may annotate said image stream with conditions believed pertinent to said user for presentation as an overlay adapted for presentation over a medical image display system;
    connecting with the medical image processing system a user interface comprising a keypad, keyboard, mouse or pointing device, or touchscreen interface—wherein a surgical camera system captures medical images transferred by a wired or wireless communication link to a medical image processing system for desired image processing, wherein the medical image processing system transmits a modulating wavelength setting to a light source system;
    performing in combination with operation of the medical image processing system an additional operation of the surgical camera system with respect to the image stream;
    combining all available video signals under control of the medical image processing system to generate an output of a surgical operation for presentation over the medical image display system;
    providing a medical image display system under control of said medical image processing system comprising, a display selected from the group consisting of a plasma display, a Liquid Crystal Display (LCD), and a Light Emitting Diode (LED) display, wherein said medical image display system displays historic medical procedure images obtained in connection with spectroscopy assisted surgical procedures to enable said user to make real time decisions based on prior historic conditions; and
    providing a light source of a wavelength output varied from a lower wavelength to an upper wavelength, wherein said wavelength variation is repeated until a particular wavelength setting is determined for the procedure under consideration so that said medical image display system, under control of and responsive to said medical image processing system may facilitate surgical procedures being performed by a surgeon; and
    storing, via said medical image processing system, a plurality of predetermined wavelengths, ranges of wavelengths, and combinations of wavelengths and intensities that are known to be optimal for visualizing a specific organ, tissue, or area of interest (AOI) and are provided as predetermined settings based on said user's real-time AOI.

7. The method according to claim 6 wherein a first number of visible edges may be determined for a first image associated with a first wavelength setting, a second number of visible edges may be determined for a second image associated with a second wavelength setting, and a successive number of visible edges may be determined where in the number of edges for the different images associated with each wavelength setting may be compared to one another to determine a wavelength setting for the procedure under consideration.

8. A method according to claim 7 wherein the image associated with the wavelength setting is the setting with the largest number of visible edges.

* * * * *